(12) United States Patent
Slater

(10) Patent No.: US 7,867,227 B2
(45) Date of Patent: Jan. 11, 2011

(54) BIPOLAR CARDIAC ABLATION SYSTEM AND METHOD

(76) Inventor: A David Slater, 14 River Hill Rd., Louisville, KY (US) 40207

( * ) Notice: Subject to any disclaimer, the term of this patent is extended or adjusted under 35 U.S.C. 154(b) by 874 days.

(21) Appl. No.: 11/677,592

(22) Filed: Feb. 22, 2007

(65) Prior Publication Data

US 2008/0208186 A1 Aug. 28, 2008

(51) Int. Cl.
*A61B 18/14* (2006.01)
(52) U.S. Cl. ...................................................... 606/41
(58) Field of Classification Search .................. 606/41, 606/48–50
See application file for complete search history.

(56) References Cited

U.S. PATENT DOCUMENTS

| | | | |
|---|---|---|---|
| 5,836,947 A | 11/1998 | Fleischman et al. | |
| 5,885,278 A | 3/1999 | Fleischman | |
| 5,910,129 A | 6/1999 | Koblish et al. | |
| 6,071,279 A * | 6/2000 | Whayne et al. | 606/41 |
| 6,120,496 A * | 9/2000 | Whayne et al. | 606/1 |
| 6,464,699 B1 * | 10/2002 | Swanson | 606/41 |
| 6,673,071 B2 | 1/2004 | Van Dusseldorp et al. | |
| 6,706,039 B2 | 3/2004 | Mulier et al. | |
| 6,832,996 B2 | 12/2004 | Woloszko et al. | |
| 6,866,662 B2 | 3/2005 | Fuimaono et al. | |
| 6,869,431 B2 | 3/2005 | Maguire et al. | |
| 6,887,238 B2 * | 5/2005 | Jahns et al. | 606/41 |
| 6,904,303 B2 | 6/2005 | Phan et al. | |
| 6,939,349 B2 | 9/2005 | Fleischman et al. | |
| 6,962,589 B2 | 11/2005 | Mulier et al. | |
| 7,029,471 B2 | 4/2006 | Thompson et al. | |
| 7,041,095 B2 | 5/2006 | Wang et al. | |
| 7,063,682 B1 | 6/2006 | Whayne et al. | |

(Continued)

FOREIGN PATENT DOCUMENTS

EP 0868922 10/1998

(Continued)

OTHER PUBLICATIONS

Haissaguerre M, Jais M, Shah D. Spontaneous Initiation of Atrial fibrillation by Ectopic Beats Originating in the Pulmonary Veins. The New England Journal of Medicine 1998; 339:659-66, US.

(Continued)

*Primary Examiner*—Linda C Dvorak
*Assistant Examiner*—Benjamin Lee
(74) *Attorney, Agent, or Firm*—Alexander P. Brackett; Middleton Reutlinger

(57) ABSTRACT

An apparatus for bipolar radio frequency ablation of heart tissue includes a flexible epicardial lead having an interior surface along a portion thereof comprising an electrically conductive surface to be placed in contact with tissue to be ablated. Additionally, the epicardial lead includes an integral fastener disposed proximate a distal end thereof and a sliding lock collar having an aperture therein through which said epicardial lead passes. A complementary fastener may be secured thereto for engaging the fastener of said epicardial lead, thereby securing said lead in place around tissue to be ablated. The apparatus further includes an endocardial ablating lead placed in the left atrial chamber via transfemoral insertion for conduction of radio frequency energy between the ablating lead and the ablating surface of the epicardial lead.

14 Claims, 17 Drawing Sheets

U.S. PATENT DOCUMENTS

| | | |
|---|---|---|
| 7,081,114 B2 | 7/2006 | Rashidi |
| 7,087,053 B2 | 8/2006 | Vanney |
| 7,089,063 B2 | 8/2006 | Lesh et al. |
| 7,104,990 B2 | 9/2006 | Jerkins et al. |
| 7,125,409 B2 | 10/2006 | Truckai et al. |
| 7,156,845 B2 | 1/2007 | Mulier et al. |
| 2004/0220560 A1* | 11/2004 | Briscoe .................. 606/32 |
| 2005/0267460 A1 | 12/2005 | Roop et al. |
| 2006/0015165 A1 | 1/2006 | Bertolero et al. |
| 2006/0461237 | 7/2006 | Cawthra, Jr. |

FOREIGN PATENT DOCUMENTS

| | | |
|---|---|---|
| EP | 1042990 | 10/2000 |
| WO | 2004043272 | 5/2004 |
| WO | 2007001981 | 1/2007 |

OTHER PUBLICATIONS

Cox JL, Boineau JP, Schuessler RB et al. Modification of the Maze Procedure for Atrial Flutter and Atrial FibrillationII. Sugical technique of the maze III procedure. Journal Thoracic Cardiovascular Surgery 1995; 110: 485-95, US.

Prasad S, Maniar H. Camillo C et al. The Cox maze III Procedure for Atrial Fibrillation: Long-term Efficacy in Patients Undergoing Lone Versus Concomitant Procedures. Journal Thoracic and Cardiovascular Surgery 2003; 126: 1822-7, US.

McCarthy PM. Gillinov AM, Castle C et al. The Cox Maze Procedure: The Cleveland Clinic Experience: Seminars in Thoracic and Cardiovascular Surgery 2000; 12:25-9, US.

Schaff HV, Dearani JA, Daly RC et al. Cox Maze Procedure for Atrial Fibrillation: Mayo Clinic Experience: Seminars in Thoracic and Cardiovascular Surgery 2000; 12:30-7, US Gaynor SL, Diodato MD, Prasad SM et al. A Prospective, Prospspective Single-center Trial of a Modified Cox Maze Procedure with Bipolar Radiofrequency Ablation. Journal Thoracic and Cardiovascular Surgery 2004; 124: 535-44, US.

Oral H, Papphone C, Chugh A et al. Circumferential pulmonary vein ablation for chronic atrial fibrillation. New England Journal Medicine 2006; 354: 934-41, US.

Cappato R, Calkins H, Chen S, et al. Worldwide Survey on Method Efficacy, and Safety of Catheter Ablation for Human Atrial Fibrillation. Circulation 2005; 111:1100-5, US.

Oral H, Scharf C, Chugh A et al. Catheter Ablation for Paroxysmal Atrial Fibrillation: Segmental Pulmonary Vein Ostial Ablation Versus Left Atrial Ablation. Circulation 2003; 108:2344-60, US.

Pappone C, Oreta G, Olamberti F, et al. Catheter Ablation of Paroxysmal Atrial Fibrillation Using a 3D Mapping System. Circulation 1999; 100:1203; 8, US.

Wazni OM, Marrouche NF, Martin DO et al. Radiofrequency Ablation vs. Antiarrhythmic Drugs as First Line Treatment of Symptomatic Atrial Fibrillation: a Randomized Trial JAMA 2005; 293: 2634-40, US.

Oral H, Knight BP, Tada et al. Pulmonary Vein Isolation for Paroxysmal and Persistent Atrial Fibrillation. Circulation 2002; 105: 1077-81, US.

Chen MS, Marrouche NF. Khaykin Y et al. Pulmonary Vein Isolation for the Treatment of Atrial Fibrillation in Patients with Impaired Systolic Function. Journal of the American College of Cardiology; 2004;43:1004-9.

Langberg J, Lee MA, Chin ME et al. Radiofrequency Catheter Ablation: the Effect of Electrode Size on Lesion volume in Vivo. Pace 1990; 13: 1242-8, US.

Gillinov AM, Pettersson G. Rive TW. Esophageal Injury During Radiotrequeoev Ablation for Atrial Fibrillation. Journal Thoracic and Cardiovascular Surgery 2001; 122: 1239-40, US.

Mohr FW, Fabricius AM, Falk V et al. Curative Treatment of Atrial Fibrillation with Intraoperative Radiotrequency Ablation: Short Term and Mid Term Results—Journal Thoracic and Cardiovascular Surgery 2002: 123: 919-27.

Jahangiri M, Graeme W, Mandai, K et al. Current Strategies in the Management of Atrial Fibrillation. Annals Thoracic Surgery 2006; 82: 357-64, US.

Prasad SM, Maniar HS. Diodato MD et al. Physiological Consequences of Bipolar Radiofrequency Energy on the Atria and Pulmonary Veins: a Chronic Animal Study. Annals Thoracic Surgery 2003;76: 836-42, US.

Mack CA, Milia F. Wilson K et al. Surgical Treatment of Atrial Fibrillation Using Argon-Based Cryoablation During Concomitant Cardiac Procedures. Circulation 2005;122(suppl I): I-1-I-6, US.

Gammie JS, Laschinger JC, Brown JM et al. A Multi-Institutional Experience with the CryoMaze Procedure. Annals Thoracic Surgery 2005; 80: 876-80, US.

Gillinov, AM, Bhavani S. Blackstone EH et al. Surgery for Pennanent Atrial Fibrillation: Impact of Patient Factors and Lesion Set. Annals Thoracic Surgery 2006; 82: 502-514.

Williams M, Knaut M, Berube D. Application of Microwave Energy in Cardiac Tissue Ablation: from in Vitro Analysis to Clinical Use. Annals Thoracic Surgery 2002:74: 1500-5, US.

Knaut M, Tugtekin S, Spitzer S. Combined Atrial Fibrillation and Mitral Valve Surgery Using Microwave Technology. Seminar Thoracic Surgery 2006; 81: 1325-31, US.

Pruitt JC. Lazzara RR. Dworkin GH et al. Totally Endoscopic Ablation of Lone Atrial Fibrillation: Initial Clinical Experience. Annals Thoracic Surgery 2006; 81: 1325-31, US.

Ninet J. Roques X. Seitelberger R et al. Surgical Ablation of Atrial Fibrillation with, Off-pump, Epicardial, High-Intensity Focused Ultrasound: Results of a Multicenter trial. Journal Thoracic and Cardiovascular Surgery 2005; 130:803. US.

* cited by examiner

BIPOLAR CARDIAC ABLATION SYSTEM AND METHOD

FIELD OF THE INVENTION

The invention disclosed and claimed herein pertains generally to a system and method of treatment for atrial fibrillation (AF) in humans. More specifically, the present invention provides a minimally invasive system and method for the delivery of bipolar radio frequency energy through the left atrial wall for the ablation of tissue and concomitant treatment of atrial fibrillation. The invention comprises an epicardial lead system and an endocardial electrical catheter designed for thoracoscopic and transvenous insertion for the delivery of bipolar radio frequency energy to create a line of scarring, thereby creating an electrical signal blockade around the pulmonary veins. The instant invention also provides for the creating of a second line of ablated tissue connecting the line of scar around the pulmonary veins to the mitral valve annulus. The invention will provide a means for application of bipolar radio frequency ablation for patients with intermittent, persistent or chronic atrial fibrillation.

BACKGROUND OF THE INVENTION

Atrial fibrillation (AF) is the most common clinically important cardiac arrhythmia. The arrhythmia is thought to result from two mechanisms. The first is a "trigger" site proximate the heart that stimulates an abnormal electrical signal that is propagated through the atrial walls. Some researchers have concluded that paroxysmal AF is induced by triggers in and adjacent to the pulmonary veins and their connection to the atrial wall in 90% of cases.

The second mechanism is a cardiac re-entry abnormality in conduction that allows and perpetuates the abnormal conduction within the atrial wall. Based on extensive animal studies in the 1980's, it has been postulated that AF resulted from the presence of a macro re-entrant circuit in the atria. These studies and others lead to the development of the Cox maze surgical procedure for the treatment of AF in 1987. The maze procedure consists of a series of transmural incisions in the atrial wall and cryoablation lesions to prevent the development of the macro re-entry circuit. Ablation results in the destruction of some portion of the tissue in the atrial wall thereby providing a portion of ablated tissue having a high electrical resistance to prevent the undesirable propagation of abnormal electrical signals in the heart.

Many clinical studies have documented the long term success of the Cox maze procedure in the restoration of sinus rhythm and elimination of AF, the preservation of atrial function, and the elimination of stroke caused by cerebral emboli. Due to the technical demands of this procedure, it was only used in a limited number of patients and less demanding and less invasive procedures were sought. Accordingly, some prior art AF treatment techniques utilize a bipolar radio frequency clamp device to create lines of ablated tissue through transmission of radio frequency energy through the atrial wall to replace many of the incisions of the "cut and sew" maze procedure. This technique resulted in success rates similar to the Cox maze surgical procedure. With the demonstration that creation of lines of electrical block in atrial tissue could be effective in treating AF, a wide variety of energy sources and multiple surgical approaches to their application have been applied to treat AF. The ideal procedure achieves transmural lines of injury and conduction block in atrial tissue, causes no damage to neighboring structures, and is applied in a minimally invasive fashion.

Catheter ablation techniques for AF treatment applied through a transfemoral access and transeptal approach to the left atrium presently provide the least invasive technique. Catheter ablation using radio frequency energy transmission has been applied with varying success rates. Success rates of 45-85% utilizing this approach have been reported in patients without structural heart disease. However, patients with chronic AF typically receive temporary antiarrhythmic drug therapy after an ablation procedure and often require one or more cardioversions or ablations to restore sinus rhythm. These are confounding variables that may inflate the actual efficacy of these prior art catheter ablation techniques. Follow up data on these patients may vary with the means of data collection and because AF may be asymptomatic, these factors may also contribute to over estimation of success rates.

An AF treatment technique utilizing an endocardial application of unipolar radio frequency energy has been employed but is subject to two significant complications. It has proven quite difficult to determine the energy necessary to create transmural lesions in atrial tissue of varying thickness. Accordingly, perforation of the atrial wall can occur with bleeding and tamponade as well as perforation of adjacent structures, most notably the esophagus. Additionally, the application of unipolar radio frequency energy in the pulmonary veins can result in their constriction with resultant pulmonary vein stenosis and its attendant complications.

Some bipolar energy delivery systems have also been attempted in the art to provide both epicardial and endocardial therapy for AF and as such, afford some advantages over prior art techniques. With bipolar energy application, the targeted tissue receives just enough energy to produce a transmural lesion which can significantly shorten ablation time. It also decreases thermal spread and thus reduces the chances of injury to adjacent structures. Impedance changes measured utilizing various electrical sensing mechanisms at the time of ablation aid in the precise delivery of energy necessary to predictably create transmural lesions.

The premise for success of the maze procedure is complete block of electrical transmission across the line of incision or ablation. Success rates of 90-95%—similar to the "cut and sew" maze procedure—have been achieved with bipolar radio frequency ablation techniques, which require an open heart cardiac procedure in conjunction with cardiopulmonary bypass and cardiac arrest. Similar excellent results have been reported with the use of cryotherapy, again requiring an open cardiac procedure with cardiac arrest and the addition of lines of ablation as described in the "cut and sew" maze procedure. These prior art procedures, while efficacious, are undesirable due to the invasive approach required for the treatment, with its concomitant risks.

Other prior art surgical procedures to provide a less invasive approach have been utilized as well. Energy sources including radio frequency, microwave, and cryotherapy used in an open heart procedure have produced results similar to the "cut and sew" maze procedure as described above, but have been less successful or unproven in a minimally invasive approach.

A variety of clamp-type devices have been employed in a minimally invasive approach. These devices are typically positioned around the pulmonary veins thence secured tightly in place and provide electrically conductive surfaces that contact the atrial wall. The clamp devices create lesions by application of energy across two thicknesses of atrial wall, and often require as many as three of four applications to provide transmural lines of ablation.

Because the circulating blood within the left atrium acts as a heat sink, application of thermal energy, whether hot or cold, (such as cryotherapy) in an epicardial approach does not produce reliable and consistent transmural lesions in the atrial wall in a beating heart.

While reasonable success rates have been reported for paroxysmal AF with pulmonary vein encircling lesions alone, additional lines of ablation are necessary to match the success rates of the "cut and sew maze" procedure in persistent or chronic AF. While the number and pattern of lines from the original "cut and sew" maze procedure that are required to increase the success rate to 90% and above are the subject of debate, the addition of a line of ablation from the pulmonary vein encircling line to the mitral valve annulus has been shown to enhance the success rate of the procedure. Clamp devices for the delivery of bipolar radio frequency ablation can not be used to create this line and many of the other lines of the maze procedure in a minimally invasive approach.

Some prior art techniques utilize microwave energy applied through an epicardial device placed on the atrial wall in an open heart epicardial procedure with success rates of 70-90%. Minimally invasive use of microwave energy introduced through standard thoracoscopic techniques and applied in an epicardial approach have also been attempted.

Another prior art technique utilizes high frequency ultrasound ablation of AF used through an open sternotomy. Use of this technique with a mini-thoracotomy approach has also been disappointing with success rates of 50-70%.

Based on the foregoing, there is a need for an AF treatment technique and apparatus that combines a minimally invasive surgical approach with a bipolar energy delivery system for both enhanced efficacy in AF treatment and swift patient recovery.

SUMMARY OF THE INVENTION

The invention described herein will take advantage of the application of bipolar radio frequency energy to the atrial wall of a heart in a novel manner. A plurality of ablating surfaces and the energy applied therethrough will be in intimate contact with the same portion of endocardial and epicardial surfaces of the atrial wall to create consistent transmural lesions along the atrial wall. Additionally, because the energy source is bipolar there is minimal chance for excess dispersion of heat to surrounding or adjacent structures.

The measurement of electrical impedance as used in currently available bipolar AF treatment devices in conjunction with the present invention will aid in administration of only the requisite amount of energy required for tissue ablation and assessment of transmurality. The apparatus of the present invention will permit the creation of an ablation line from the pulmonary vein encircling line to the mitral valve annulus, which has been shown to increase success rates particularly in persistent or chronic AF. The apparatus and method disclosed herein will be minimally invasive and will employ a unilateral thoracoscopic and transfemoral venous surgical approach to the areas to be ablated.

The present invention is particularly suited for ablation of cardiac tissue to inhibit atrial fibrillation. An epicardial lead is provided having a plurality of ablating surfaces along its length for delivery of bipolar radio frequency energy to a targeted line of tissue. The epicardial lead is delivered to the targeted area through a 3 cm. right thoracic incision utilizing known in the art thoracoscopic surgical techniques.

The epicardial lead is passed between the right superior pulmonary vein and the right pulmonary artery to enter the transverse sinus. The epicardial lead includes a tip portion including a detachable loop that is retrieved by a surgeon using standard thoracoscopic techniques through the oblique sinus between the right inferior pulmonary vein and the inferior vena cava.

The epicardial lead may further include a mitral valve slide which engages the epicardial lead at a plurality of interior surfaces and through which the epicardial lead passes. The mitral valve slide is moved with the epicardial lead until it is positioned proximate the left inferior pulmonary vein. The mitral valve slide may further include a conducting surface contacting the atrial wall for providing a continuous line of ablation between the epicardial lead ablating surface and a mitral valve lead as discussed herein below. Once the mitral valve slide is accurately positioned, the epicardial lead is advanced to encircle the pulmonary veins while the mitral valve slide remains stationary.

The mitral valve slide includes a mitral valve lead passage that comprises a right angle bend for guiding a mitral valve lead inserted therethrough to cross the atrioventricular groove. The mitral valve lead is typically a wire or element capable of conducting electrical energy and flexible enough to travel through the passage in the mitral valve slide. Once positioned, the mitral valve lead is held in close contact to the epicardial surface of the heart with a balloon that is inflated through an air supply catheter connected to an air supply port in the mitral valve slide. The balloon inflates in an orientation such that it forces the mitral valve lead into position proximate the left atrial wall and the atrioventricular groove. The mitral valve lead is further capable of sensing electrical activity as a function of voltage at a plurality of points along its length to assist in positioning the delivery of energy relative to the mitral valve.

The epicardial lead is locked into position by utilizing a locking collar through which the epicardial lead passes and which includes a fastener thereon. The locking collar slides forward until the fastener thereon is positioned proximate a locking fastener extending outwardly from the epicardial lead at a point near a distal end of the lead, whereon the locking fastener and lead fastener are secured together by one of a plurality of techniques. The fasteners will allow passage of a heavy gauge tie that may be secured by use of a Rummel tourniquet and a cylindrical tube to constrict the tie.

The mitral valve slide may be positioned by manipulation of push/pull controlling rods which pass along the exterior of a central portion of the epicardial lead through guides secured thereto at a plurality of points. One controlling rods may include an irrigation lumen or lumens for irrigation fluid to be delivered to an irrigation system integral to the mitral valve slide to allow smooth positioning thereof the slide and facilitate passage of the central portion of the epicardial lead as well as improve electrical contact for bipolar radio frequency ablation.

The invention further includes an endocardial lead which includes an endocardial catheter and an ablating lead capable of measuring electrical activity proximate thereto, provide delivery of radio frequency energy to targeted tissue. The ablating lead may include a folding tip that unfolds when forced out of the catheter which is designed to provide about 1 cm length of conducing surface for ablation. The endocardial lead is positioned via transfemoral insertion of the catheter and transeptal placement thereof into the left atrial chamber. In an alternative embodiment of the invention, the folding tip of the ablating lead may be controlled by slide wires connected thereto at the tip portion of the ablating lead to provide closure for insertion and removal, and 90 degree opening of the contact surface for proper endocardial contact.

Bipolar ablation is initiated by placement of the ablating lead tip against the left atrial wall interior while the epicardial lead conductive surface is positioned directly opposite the lead tip on the atrial wall exterior. The epicardial lead ablating surface may include a plurality of conducting segments of 1 cm. in length and may be sequentially activated. The epicardial lead conducting segments are then sequentially energized to conduct energy therethrough in a circular application while the conducting tip of the endocardial lead is positioned opposite each conducting segment in turn. A second application of radio frequency energy with adjacent halves of each section may be performed to ensure overlap of ablative segments.

As an example of one energy delivery device, radio frequency energy may be applied using an radio frequency generator, for example an EPT 1000 commercially available from EP Technologies, Inc. of Sunnyvale, Calif., at 20-50 watts of power at 500 KHz frequency until impedance change at the ablated tissue site plateaus.

Other objects, features and advantages of the present invention will be apparent from the detailed description of the preferred embodiments herein below taken in conjunction with the drawing Figures.

BRIEF DESCRIPTION OF THE DRAWING FIGURES

DETAILED DESCRIPTION OF THE PREFERRED EMBODIMENT(S)

Figure 1:
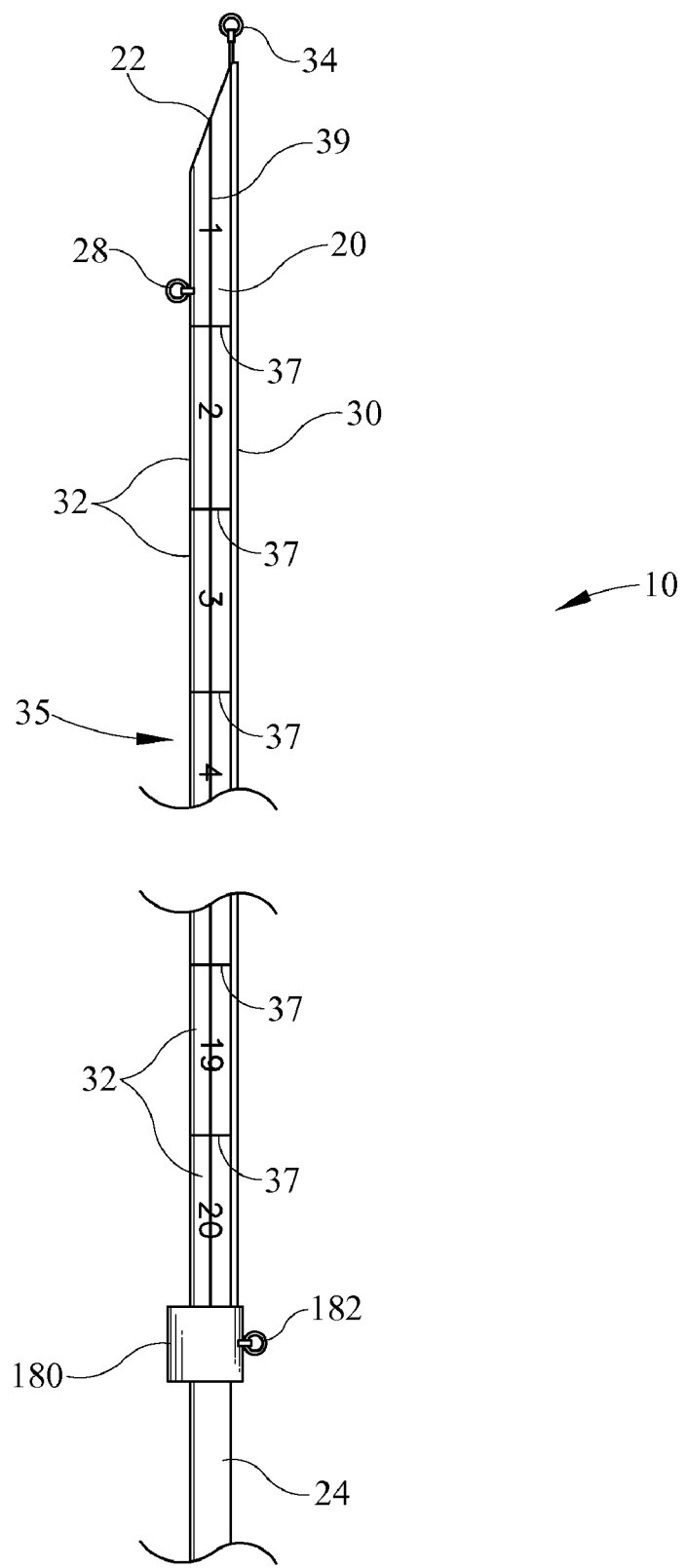
FIG. 1 is a plan view of an epicardial lead in accordance with one embodiment of the present invention.

Referring now to the drawing Figures, and in accordance with a preferred constructed embodiment of the present invention, a system 10 and method for the treatment of atrial fibrillation utilizing bipolar radio frequency ablation comprises an epicardial lead 20 having a distal end 22 and a proximal end 24 and further including a locking fastener 28 secured proximate the distal end 22 thereof Locking fastener 28 may be a loop or hook adapted to be secured to a corresponding fastener as discussed further herein below.

Epicardial lead 20 further comprises an ablating surface 30 that extends along a portion of its length and that may comprise a material that is suitable for the conduction of radio frequency electrical energy. In an alternative embodiment of the present invention, ablating surface 30 may comprise a plurality of segmented ceramic surfaces on the portion of epicardial lead 20 in contact with the targeted tissue to be ablated, wherein electrical conduction takes place in the presence of irrigation fluid supplied to the tissue. In one embodiment of the present invention, ablating surface 30 may comprise a continuous flexible metallic alloy surface capable of conducting electromagnetic energy. In any event, ablating surface 30 is further segmented into a plurality of discrete segments 32, shown in FIGS. 1-3 as numbered segments 1-20. Radio frequency energy may be supplied to any one individual conducting segment 32 through a radio frequency power generator (not shown). Suitable radio frequency power generators are known in the art and are commercially available. In a yet further embodiment of the present invention each conductive segment 32 may be further subdivided into partial segments whereby radio frequency energy may be applied to adjacent partial segments to further enhance the continuity of transmurality of the lines of conduction block created by the ablation of targeted tissue.

Epicardial lead 20 may further comprise a detachable loop 34 secured to distal end 22 thereof, to aid in positioning epicardial lead 20 prior to operation of the invention. Detachable loop 34 may be secured to epicardial lead 20 via conventional helical mating threads. Epicardial lead 20 further includes a plurality of rod guides 38 secured to the exterior thereof to engage a plurality of control rods 104 for purposes of positioning as will be discussed below.

Figure 1A:
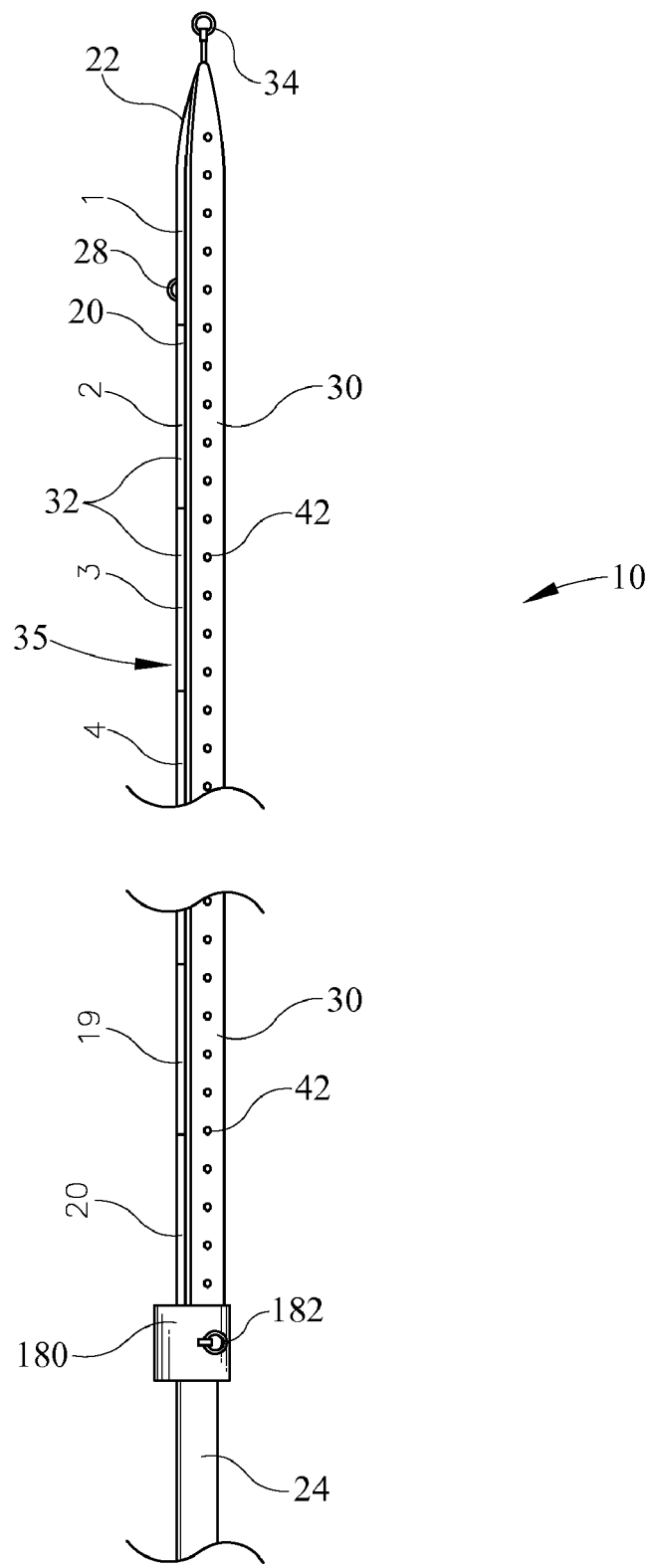
FIG. 1A is a plan view of an epicardial lead showing the conductive surface thereof in accordance with one embodiment of the present invention.

As best seen in FIGS. 4-7 epicardial lead 20 may include a central irrigation passage 40 that extends along the length of lead 20 and which may be connected to a source of irrigation fluid, for example a normal saline solution. Irrigation passage 40 may be integral to epicardial lead 20 and is in fluid communication with ablating surface 30 via a plurality of irrigation apertures 42 disposed therein as best seen in FIG. 1A, thereby providing a source of irrigation fluid to the targeted tissue being ablated. In one embodiment of the invention, irrigation passage 40 is enclosed by epicardial lead 20 and in fluid communication with apertures 42 for delivery of irrigation fluid therethrough.

Epicardial lead 20 may further comprise a mitral valve slide 100 as best seen in FIGS. 2-7. Mitral valve slide 100 includes an interior surface 101 shaped to engage an exterior surface 36 of epicardial lead 20. Mitral valve slide 100, as best seen in FIGS. 4-7 includes a plurality of control rod apertures 102 that accept an end of a plurality of flexible control rods 104. Control rods 104 are threaded through guides 38 thence securely seated in rod apertures 102 to permit a surgeon to accurately position mitral valve slide 100 by imparting a "push-pull" motion to control rods 104.

Mitral valve slide 100 further comprises a mitral valve lead passage 110 sized to accept a flexible mitral valve lead 200. Mitral valve lead 200 is constructed in much the same fashion as epicardial lead 20, except that mitral valve lead 200 comprises a plurality of conducting segments 202 only at a distal end thereof Conducting segments 202 of mitral valve lead 200, shown as segments A-D in FIGS. 6 and 7, may also be individually connected to a source of power to conduct radio frequency energy to targeted tissue. Mitral valve lead passage 110 includes an interior angled portion that guides mitral valve lead 200 to an exit aperture 112 of lead passage 110 at approximately a 90° angle to the longitudinal axis of epicardial lead 20. This feature of the present invention assists in accurate placement of mitral valve lead 200 proximate the atrioventricular groove and left atrial wall of the heart.

Figure 5:
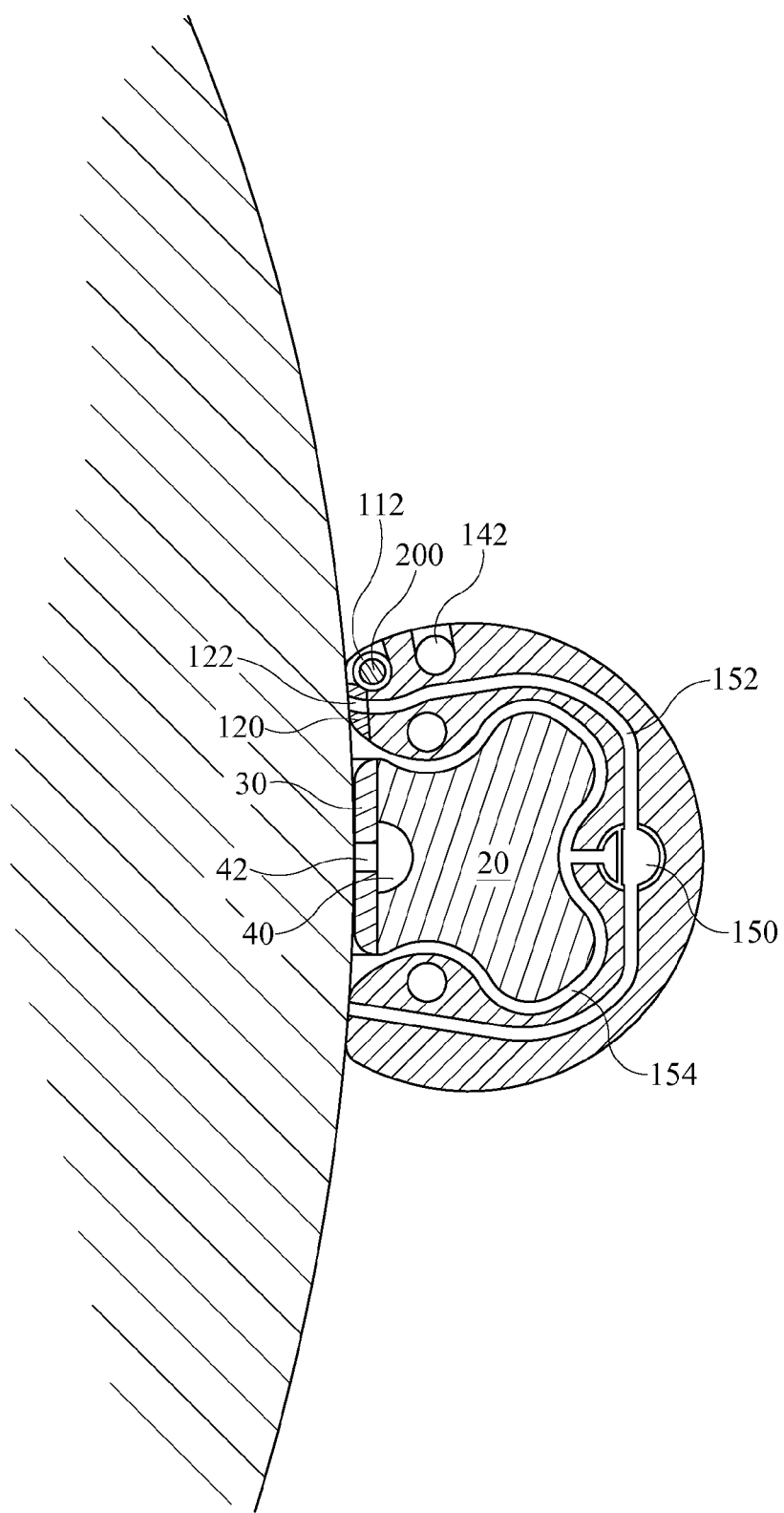
FIG. 5 is a cross-sectional view of a mitral valve slide taken along the line 5-5 of FIG. 3 in accordance with one embodiment of the present invention.
Figure 6:
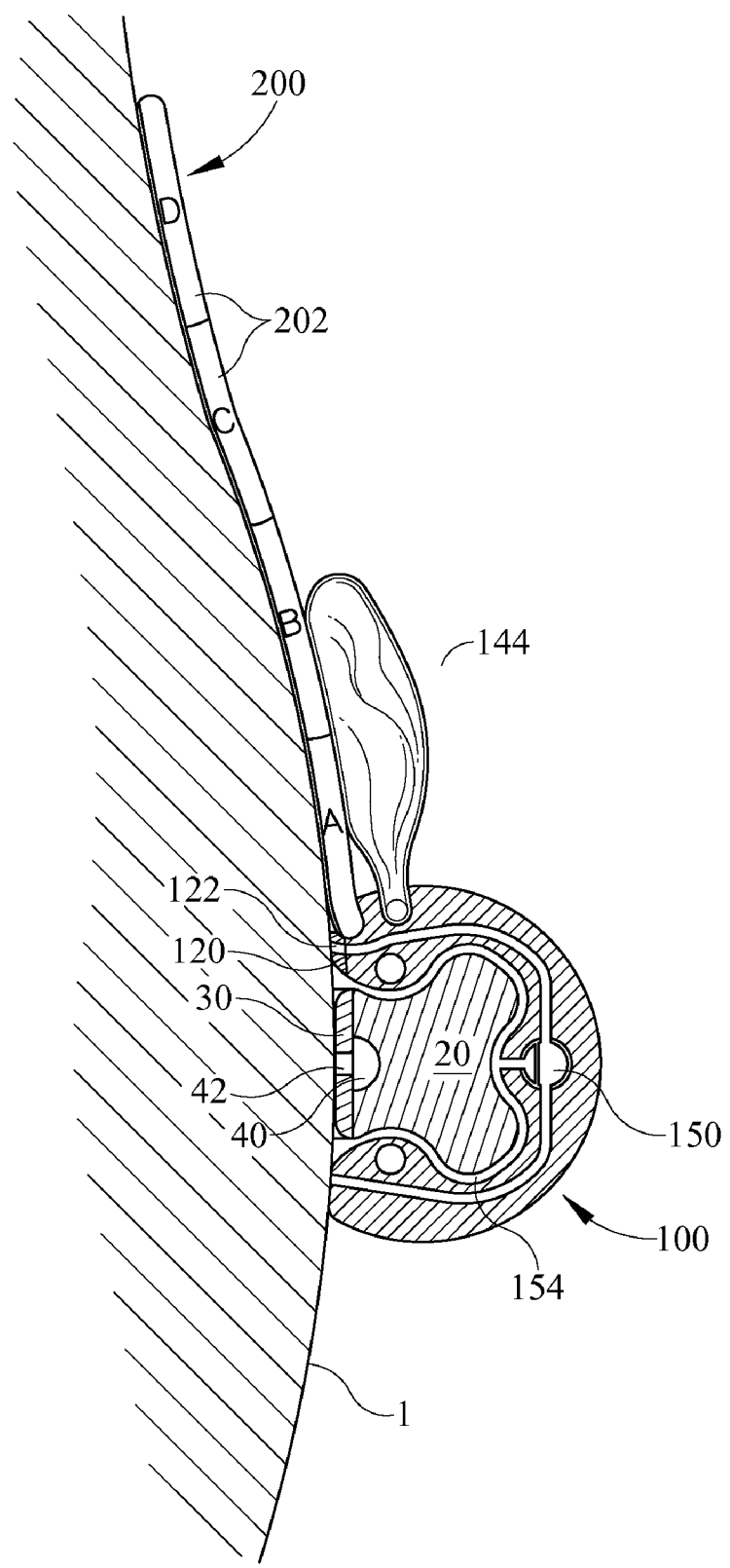
FIG. 6 is a cross-sectional view of a mitral valve slide depicting partial balloon inflation in accordance with one embodiment of the present invention.
Figure 7:
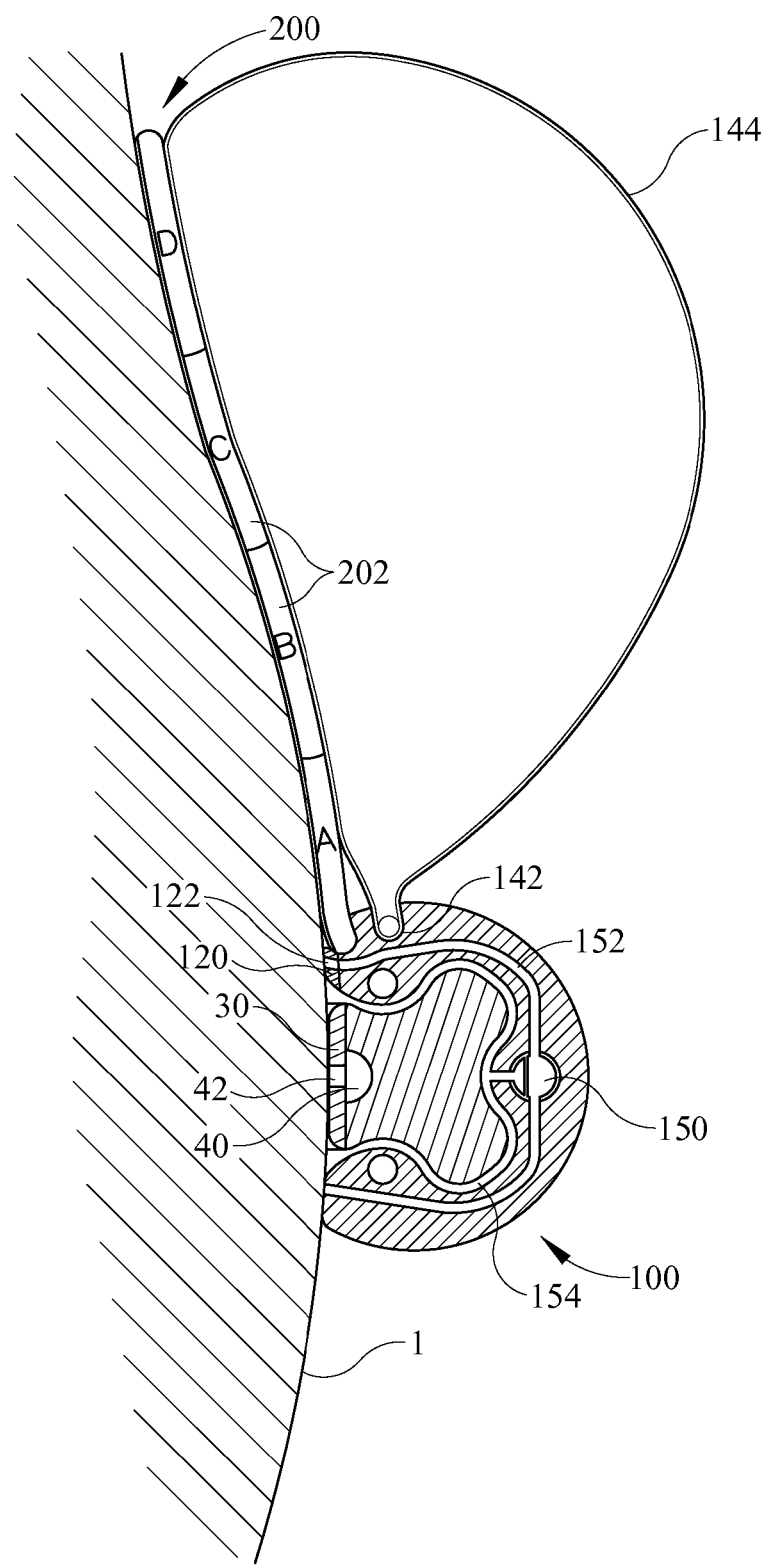
FIG. 7 is a a cross-sectional view of a mitral valve slide depicting complete balloon inflation in accordance with one embodiment of the present invention.

As seen in FIGS. 4-7 and 15, mitral valve slide 100 may additionally include an air port 140 having an entrance aperture 141 connected to a supply of compressed air and an exit aperture 142 proximate the exit aperture 112 of mitral valve lead passage 100. A surgical balloon 144 is secured in fluid communication with exit aperture 142 such that a charge of compressed air through exit aperture 142 inflates balloon 144 which then presses mitral valve lead 200 into place across the atrioventricular groove and against atrial wall 1, as best seen in FIGS. 6 and 7. This feature of the present invention provides for positive location and contact between mitral valve lead 200 and atrial wall 1, thereby enhancing transmurality of ablated tissue.

Mitral valve slide 100 also comprises a central irrigation port 150, shown in FIGS. 4-7 as a double lumen that is connected to a source of irrigation fluid via an irrigation tube 151. As best seen in FIGS. 5-7 irrigation port 150 terminates into first and second irrigation passages 152 and 154 respectively, to provide a supply of irrigation fluid to enhance the ability of the slide to move along the atrial wall for purposes of positioning as well as provide irrigation proximate the targeted tissue ablation areas. The double lumen irrigation port 150 permits irrigation fluid to be provided to either first or second irrigation passages 152, 154, or both as the needs of the procedure dictate.

As best seen in FIGS. 4-7 mitral valve slide 100 may additionally include a conducting surface 120 that extends along a portion of slide 100 that is in contact with atrial wall 1, between epicardial lead 20 ablating surface 30 and mitral valve lead 200. As best shown in FIGS. 6 and 7, mitral valve slide 100 conducting surface 120 contacts mitral valve lead 200 proximate its "A" segment, thereby permitting conducting surface 120 to be energized concomitantly with segment "A", and further providing for an uninterrupted line of ablation. Conducting surface 120 may further comprise an irrigation port 122 therein that is in fluid communication with irrigation passage 152 for supplying irrigation fluid to tissue being ablated.

Figure 8:
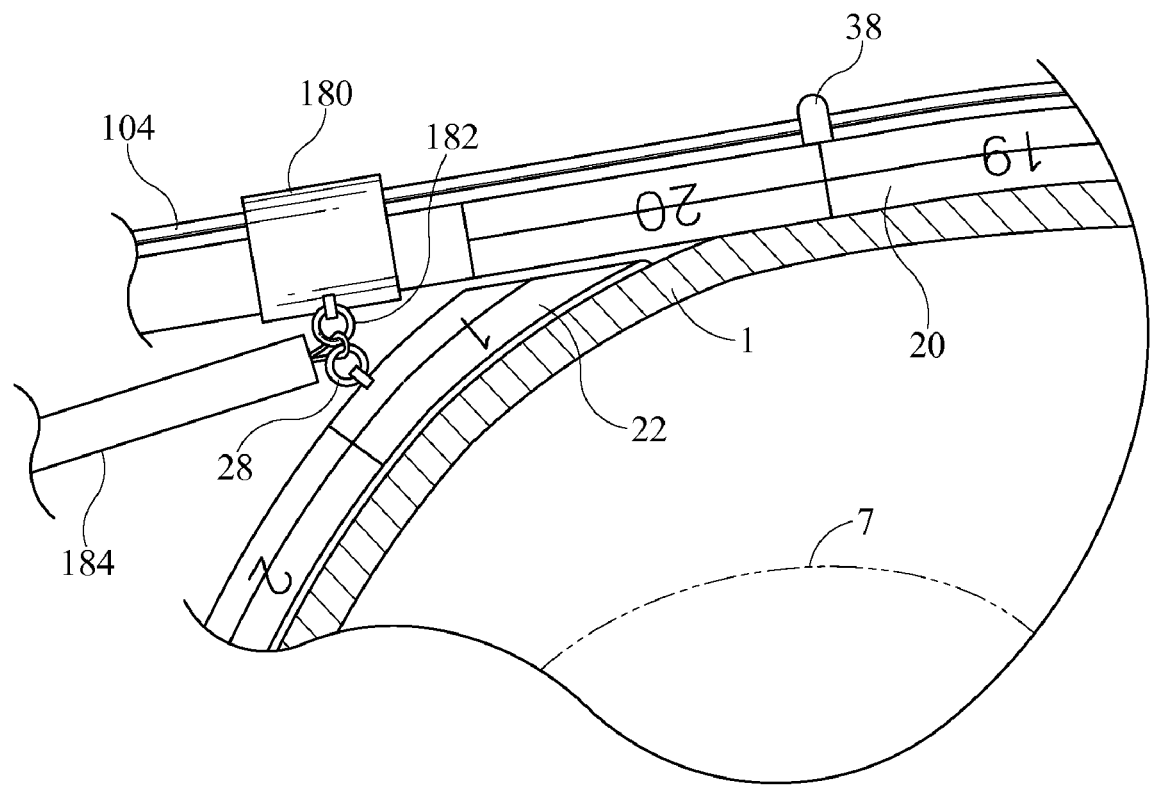
FIG. 8 is a partial view of a locking slide of the epicardial lead in accordance with one embodiment of the present invention.
Figure 9:
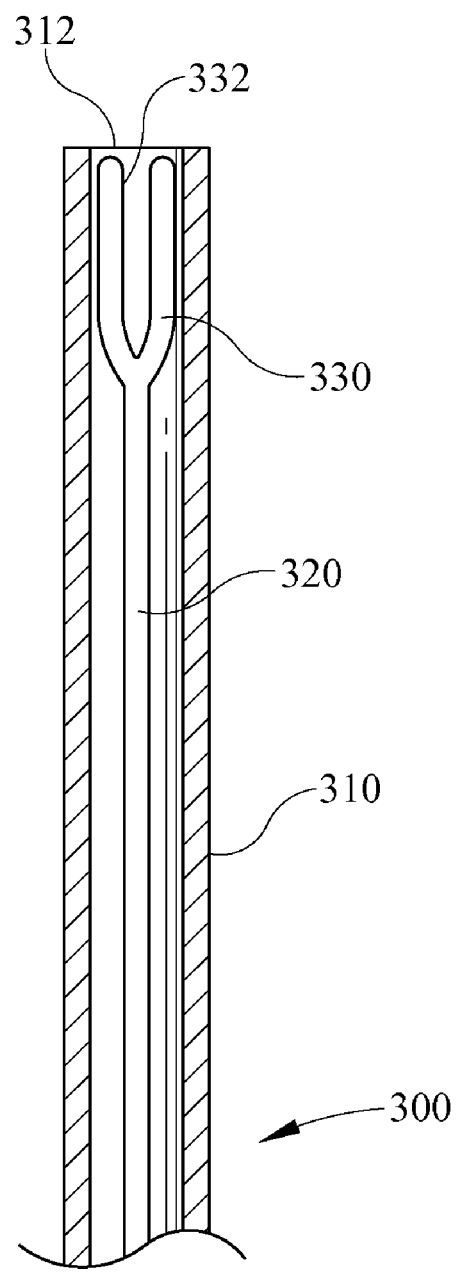
FIG. 9 is a plan view of an endocardial lead in accordance with one embodiment of the invention.
Figure 10:
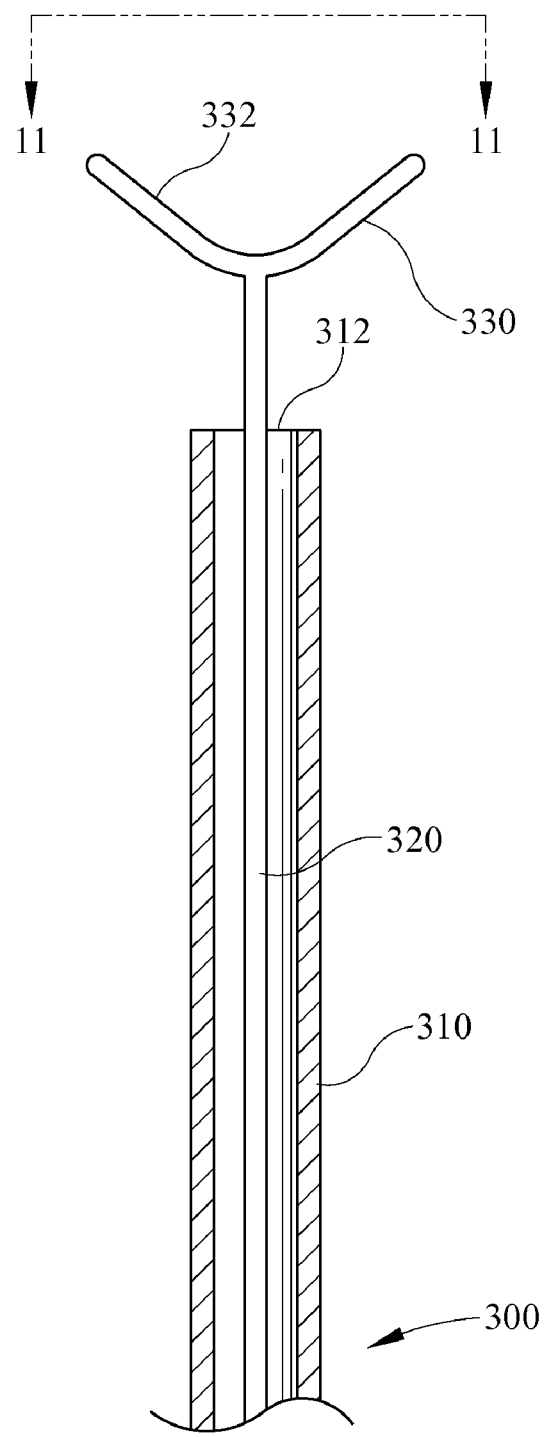
FIG. 10 is a plan view of an endocardial lead in accordance with one embodiment of the invention.

As shown in FIG. 8 the epicardial lead 20 further includes a sliding lock collar 180 through which lead 20 passes and which includes a fastener 182 for securing epicardial lead 20 in place. In operation sliding lock collar 180 is pushed longitudinally along epicardial lead 20 until fastener 182 is proximate fastener 28 of epicardial lead 20, whereupon the surgeon secures fasteners 28 and 182 together by means of, for example, a Rummel tourniquet using a heavy gauge tie, and concomitant cylindrical tube 184 and clamp 5. Thus secured, the epicardial lead 20 conductive surface 30 maintains consistent contact with atrial 1.

Referring now to FIGS. 9-14 an endocardial lead 300 comprises an endocardial catheter 310 enclosing an ablating lead 320. Endocardial catheter 310 is positioned in the left atrial chamber 2 of the heart via transfemoral insertion of the catheter 310.

Figure 11:
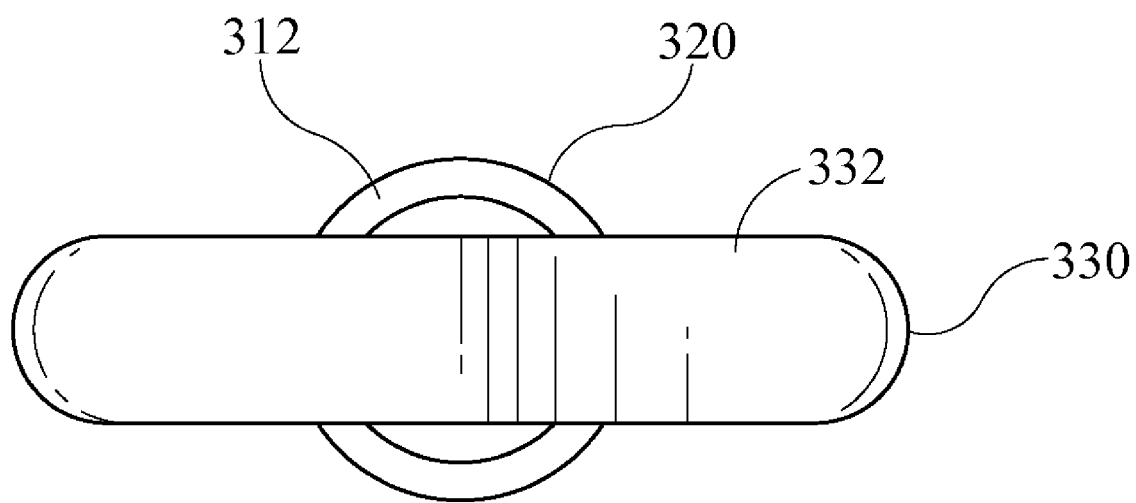
FIG. 11 is a view of an endocardial lead taken along the line 11-11 of FIG. 10 in accordance with one embodiment of the present invention.

Ablating lead 320 comprises a tip portion 330 having a conductive surface 332 for the delivery of radio frequency energy. In one embodiment of the present invention, ablating lead 320 tip portion 330 is comprised of a flexible material having shape memory, whereby tip portion 330 flexes into an "open" position as ablating lead 320 is pushed out of an end 312 of endocardial catheter 310, thus exposing conductive surface 332. This feature of the present invention obviates the need for a plurality of control wires or rods to properly position conductive surface 332 of ablating lead 320. FIG. 11 depicts a view of conductive surface 332 of ablating lead 320 in its fully open position.

Figure 12:
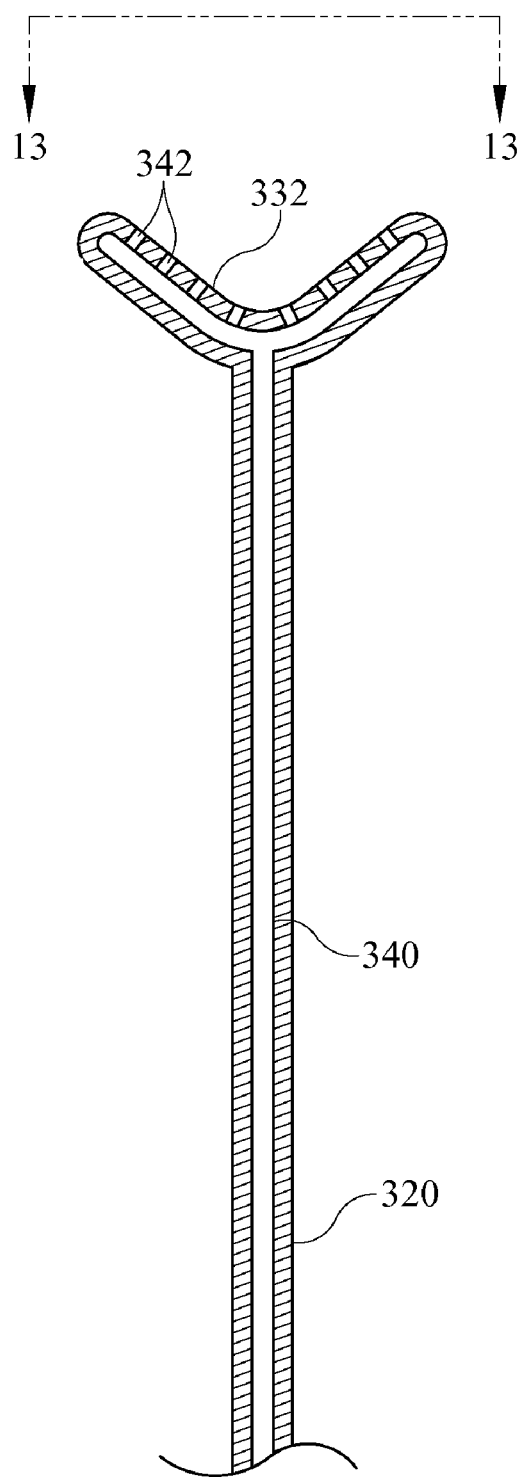
FIG. 12 is a plan view of an ablating lead in accordance with one embodiment of the present invention.
Figure 13:
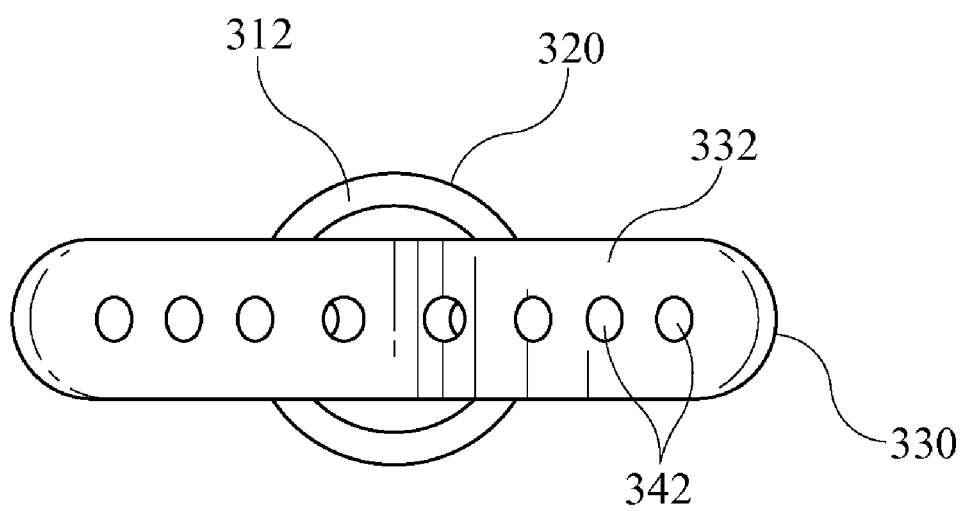
FIG. 13 is a view of an ablating lead taken along the line 13-13 of FIG. 12 in accordance with one embodiment of the present invention.

As shown in FIGS. 12 and 13, ablating lead 320 may further comprise a central lumen 340 terminating in a plurality of irrigation ports 342 disposed in conductive surface 332 of ablating lead 320. Central lumen 340 is then supplied with suitable fluid such as normal saline solution to provide irrigation to tip portion 330 during the ablation process.

Figure 14:
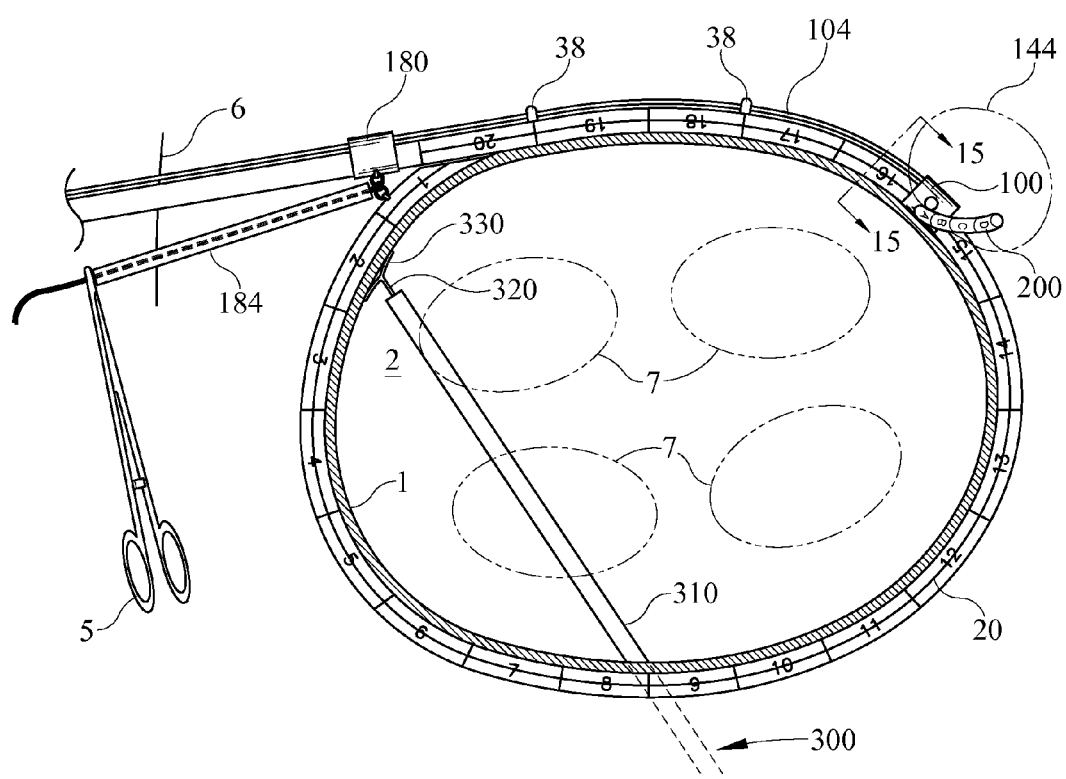
FIG. 14 is a perspective view of the system in accordance with one embodiment of the present invention.
Figure 15:
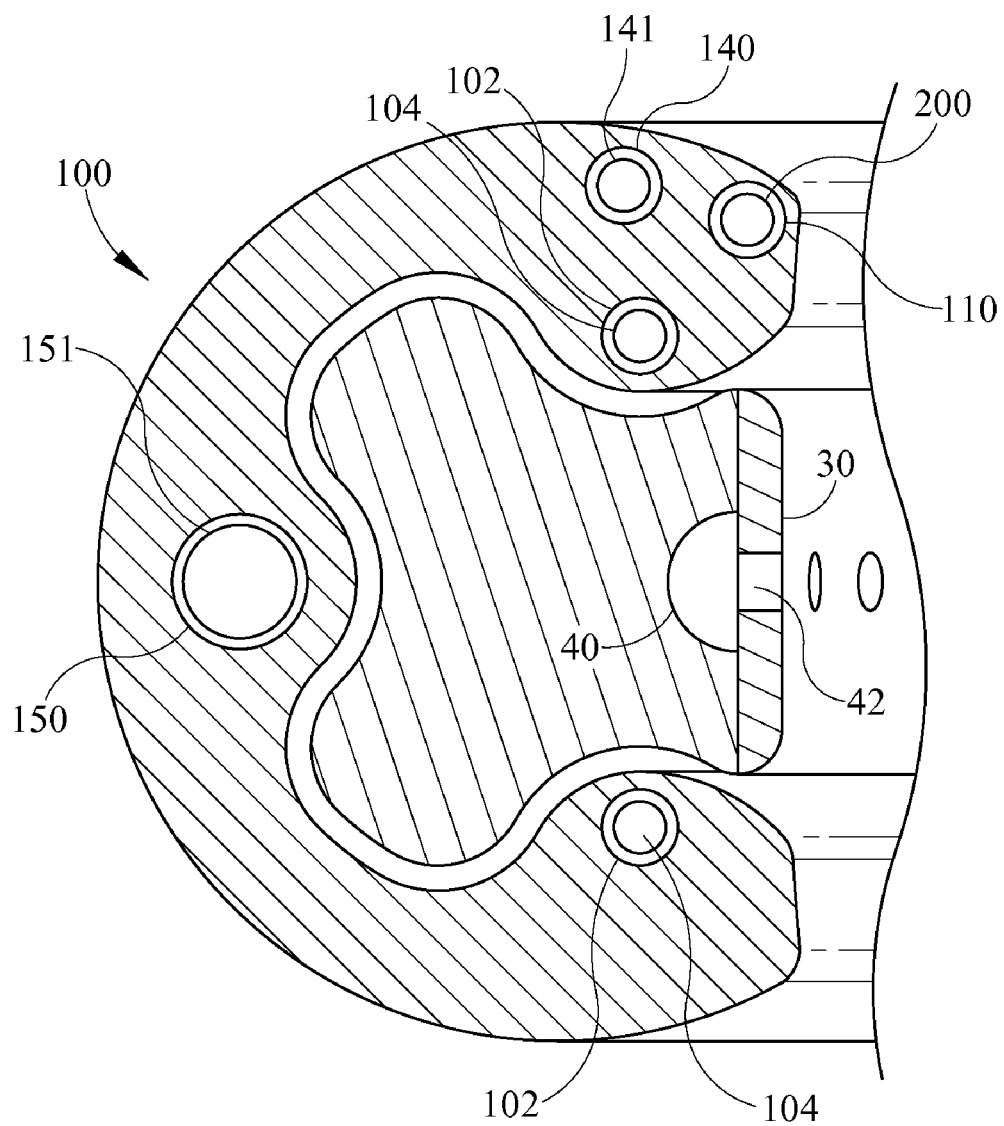
FIG. 15 is a cross-sectional view of the epicardial lead taken along the line 15-15 of FIG. 14.

FIG. 14 depicts the proper placement of both epicardial lead 20 through the chest wall 6 and endocardial lead 300 as necessary for the application of radio frequency energy from the interior of the atrial wall 1 to the exterior thereof, thereby providing for extremely consistent transmural lesions.

In a yet further embodiment of the invention, the conducting segments 32 include numbers (or other identifying markings) thereon comprised of a radiopaque material to enable a surgeon to identify each segment 32 by use of standard fluoroscopic equipment, for example a conventional x-ray machine commonly found in hybrid operating facilities with bi-planar fluoroscopy equipment or standard cardiac catheterization facilities. As best seen in FIG. 1, epicardial lead 20 may additionally have a plurality of transverse radiopaque segment dividers 37 as well as a longitudinal radiopaque line 39 thereon, to enable a surgeon to quickly view the position of epicardial lead 20 relative to ablating lead 320. This feature of the invention allows the ablating lead 320 to be precisely positioned opposite the segment 32 being energized with a minimum of effort and time. Additionally, the labeled segments 202 of mitral valve lead 200 may also comprise radiopaque markings to enable quick and accurate placement thereof during surgery.

In operation, epicardial lead 20 is placed in position around the heart by insertion through a small right thoracic incision. Epicardial lead 20 is then routed between the right superior pulmonary vein and the right pulmonary artery. Detachable loop 34 is then retrieved via access through the oblique sinus between the right inferior pulmonary vein and the inferior vena cava. Once this loop is retrieved, distal end 22 of epicardial lead 20 is routed around to meet with a central portion thereof as seen in FIGS. 2, 3, 14 and 16.

In alternative embodiments of the invention wherein epicardial lead 20 is equipped with mitral valve slide 100 epicardial lead 20 is advanced such that mitral valve slide 100 is positioned proximate the left inferior pulmonary vein. Control rods 104 are then manipulated to maintain the position of mitral valve slide 100 while epicardial lead 20 is further advanced. Detachable loop 34 is then retrieved via access through the oblique sinus between the right inferior pulmonary vein and the inferior vena cava. Distal end 22 of epicardial lead 20 is routed around to meet with a central portion thereof, as discussed herein above. Once mitral valve slide 100 is properly positioned and epicardial lead 20 is advanced and retreived, lock collar 180 is pushed forward along epicardial lead 20 until distal end 22 nests against a central portion 35 thereof, as best seen in FIG. 8. Distal end 22 of epicardial lead 20 may be shaped to closely nest with central portion 35 such that conductive surface 30 is essentially arranged in a continuous loop around the heart. This feature of the invention permits the line of ablated tissue to be nearly perfectly uniform along its entire length, thereby enhancing transmurality of lesions.

Figure 2:
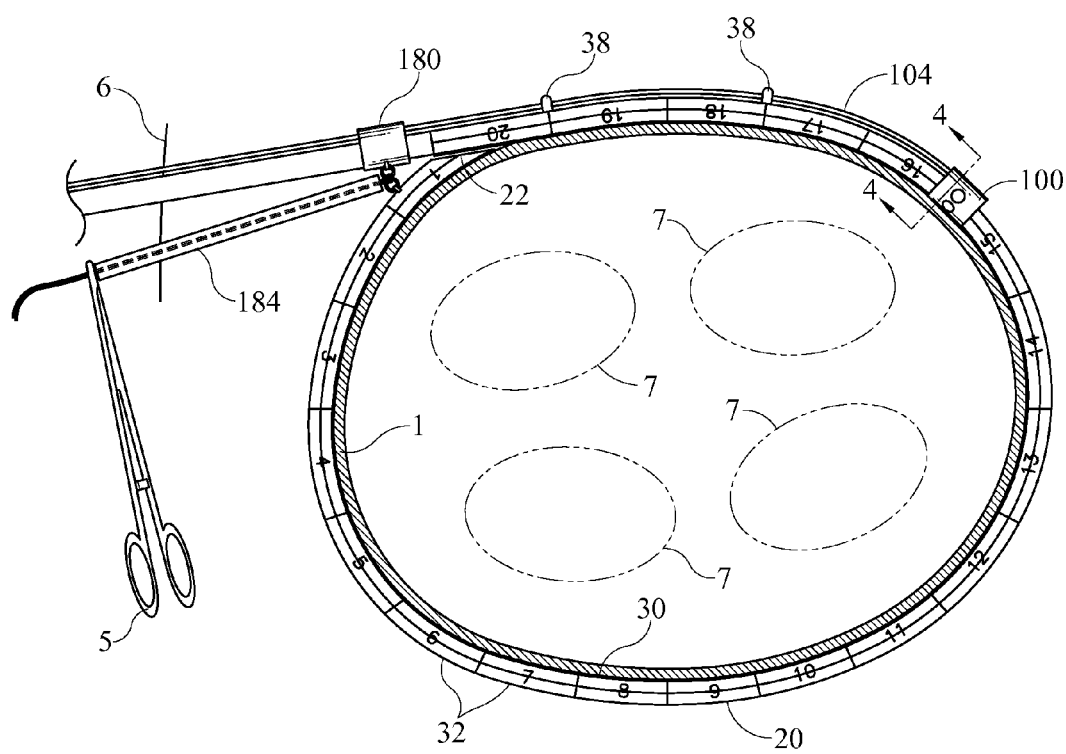
FIG. 2 is a perspective view of an epicardial lead positioned proximate the atrial wall of a heart in accordance with one embodiment of the present invention.
Figure 3:
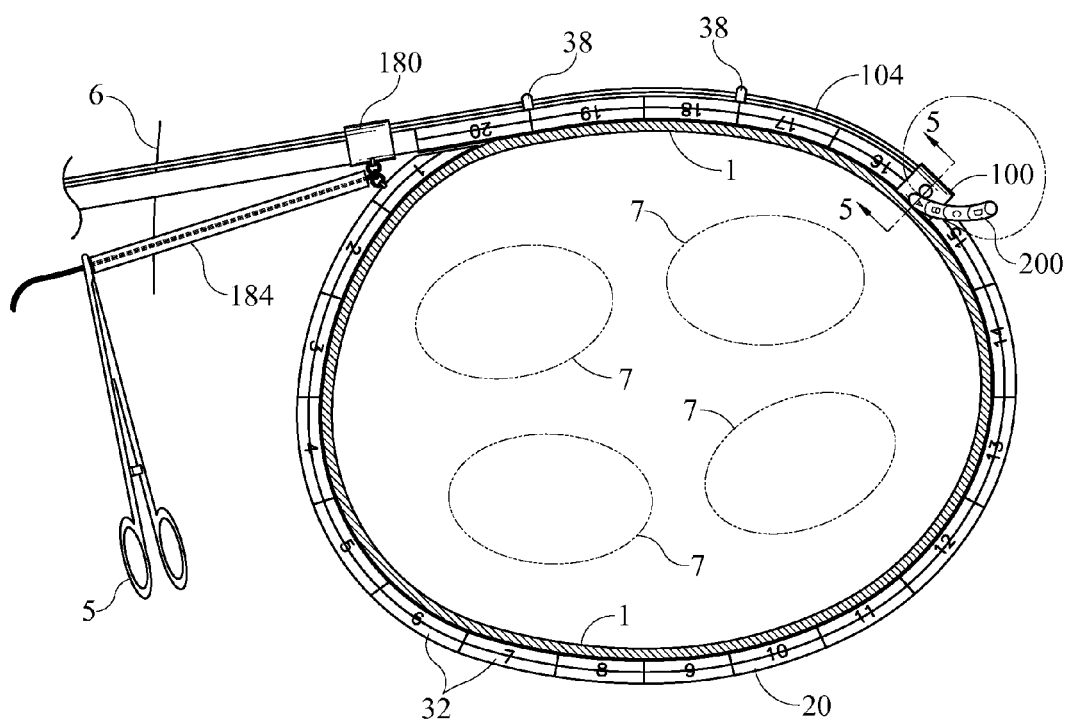
FIG. 3 is a perspective view of an epicardial lead positioned proximate the atrial wall of a heart in accordance with one embodiment of the present invention.
Figure 4:
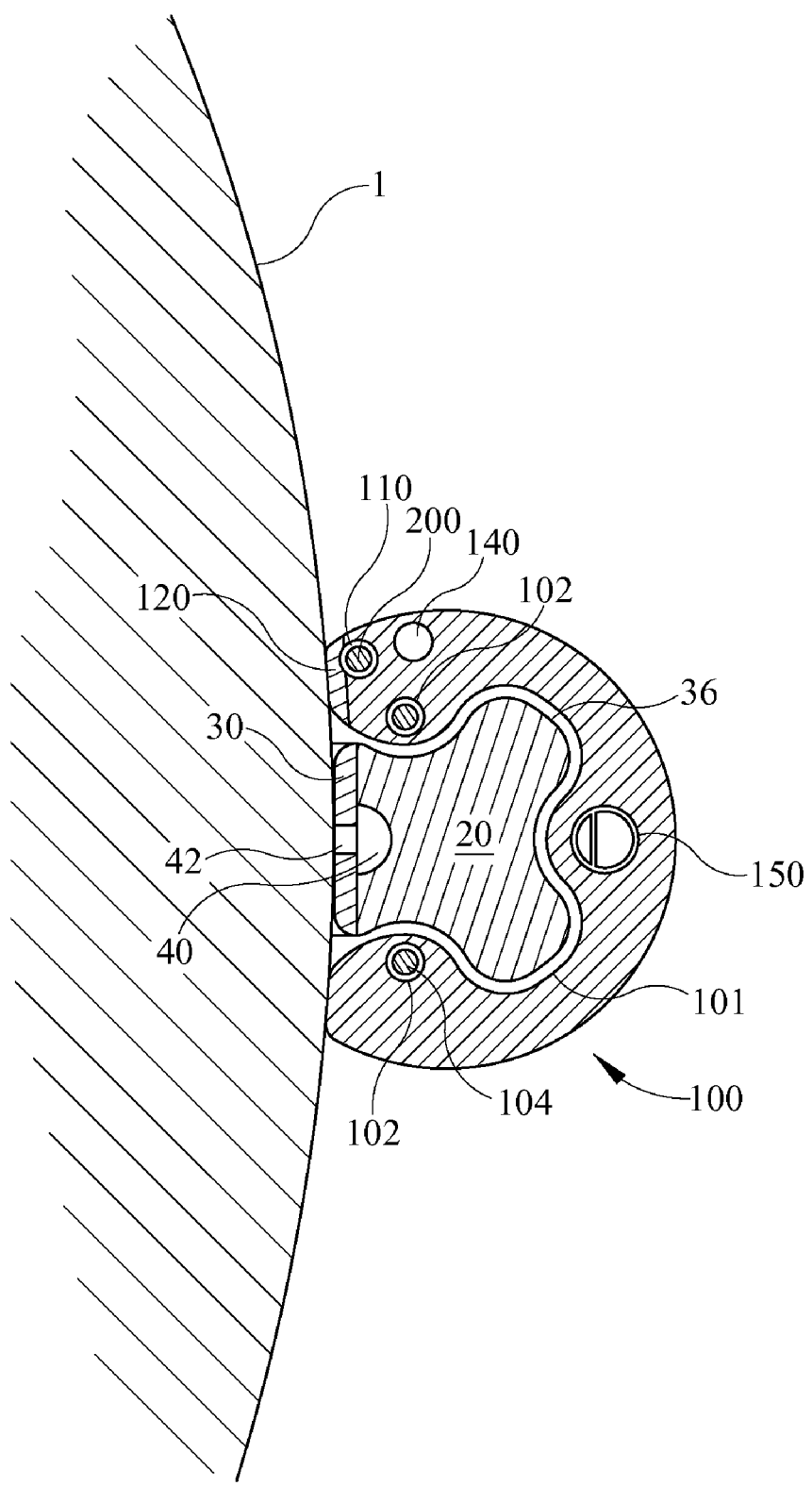
FIG. 4 is a cross-sectional view of a mitral valve slide taken along the line 4-4 of FIG. 2 in accordance with one embodiment of the present invention.

Once sliding lock collar 180 is properly positioned, fasteners 28 and 182 are secured together with a heavy gauge suture or tie, the ends of the suture or tie are threaded through cylindrical pusher 184 which is subsequently forced towards fasteners 28 and 182 to secure them together. Once so positioned, a clamp 5 is placed on the tie ends outside the chest wall 6 to secure cylindrical pusher 184 tightly in place as best seen in FIG. 2. Thus epicardial lead 20 and mitral valve slide 100 are securely positioned around pulmonary veins 7 and against atrial wall 1 prior to application of radio frequency energy application.

Additionally, endocardial catheter 310 is positioned in the left atrial chamber of the heart via conventional transfemoral insertion, whereupon ablating lead 320 is pushed out of catheter end 312 to expose tip portion 330 and ablating surface 332.

Figure 16:
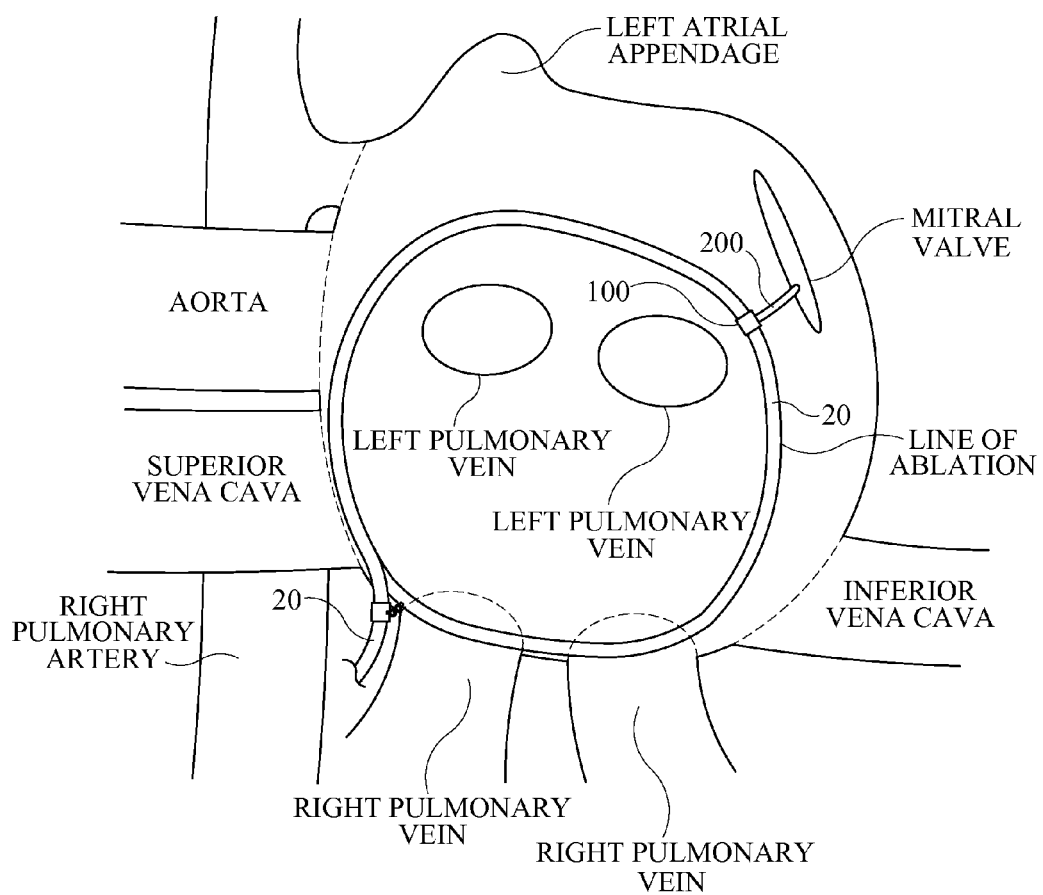
FIG. 16 is a perspective view of the system positioned for operation around the heart in accordance with one embodiment of the present invention.

Finally, as best seen in FIGS. 6 and 7 balloon 144 is inflated to bias mitral valve lead 200 against atrial wall 1 and the atrioventricular groove towards by supplying air port 140 with compressed air. FIG. 16 depicts the positioning of the epicardial 20 and mitral valve 200 leads with in a perspective view with respect to the various structures of the heart. At this point in the procedure, ablating surface 332 of ablating lead 320 is positioned directly opposite a first conducting segment 32 of epicardial lead 20 by carefully viewing the radiopaque markings thereon using standard bi-planar fluoroscopy.

Once properly positioned, a source of radio frequency energy supplied by a radio frequency generator (not shown) is connected between ablating lead 320 and first segment 32 to ablate that portion of the atrial wall therebetween. The electrical resistance measured between ablating lead 320 and first segment 32 will increase as the ablation of the tissue progresses. Once this resistance plateaus, the radio frequency energy source is disconnected (or switched off) and the ablating lead 320 is moved opposite the next segment in the sequence whereupon the foregoing process is repeated. In one embodiment of the present invention, each segment 32 may be configured to partially conduct energy so that adjacent partial segments 32 are energized sequentially, thereby enhancing the continuity of transmurality.

The measurement of electrical resistance as seen between ablating lead 320 and conductive segment 32 may be provided by one of many known in the art radio frequency generators equipped to conduct resistance measurements, which are typically accomplished by simply measuring the current flowing through the circuit while maintaining a constant voltage output.

While the present invention has been shown and described herein in what are considered to be the preferred embodiments thereof, illustrating the results and advantages over the prior art obtained through the present invention, the invention is not limited to those specific embodiments. Thus, the forms of the invention shown and described herein are to be taken as illustrative only and other embodiments may be selected without departing from the scope of the present invention, as set forth in the claims appended hereto.

I claim:

1. An apparatus for bipolar radio frequency ablation of heart tissue comprising:
    a flexible epicardial lead having an interior surface comprising an ablating surface along a portion thereof to be placed in contact with tissue to be ablated, and an integral fastener disposed proximate a distal end thereof;
    a sliding lock collar having an aperture therein through which said epicardial lead passes, and a complementary fastener secured thereto for engaging the fastener of said epicardial lead, thereby securing said lead in place around tissue to be ablated;
    a mitral valve slide having a central aperture therein through which said epicardial lead passes; and
    a mitral valve lead extending from said mitral valve slide having an electrically conductive surface thereon.

2. An apparatus for bipolar radio frequency ablation as claimed in claim 1 wherein said electrically conductive surface of said mitral valve lead has a plurality of discrete segments capable of being individually connected to a source of radio frequency energy.

3. An apparatus for bipolar radio frequency ablation as claimed in claim 2 further comprising:
    a plurality of radiopaque conductive markers spaced along said mitral valve lead discrete segments whereby said radiopaque markers are visible using standard fluoroscopic techniques.

4. An apparatus for bipolar radio frequency ablation as claimed in claim 1 wherein said mitral valve slide includes a mitral valve lead passage therein, said lead passage having an entrance aperture for inserting said mitral valve lead and an exit aperture oriented to guide said mitral valve lead proximate a left atrial wall and an atrioventricular groove of said heart tissue.

5. An apparatus for bipolar radio frequency ablation as claimed in claim 4 wherein said mitral valve slide comprises:
    an air port having an entrance aperture in fluid communication with a source of compressed air and an exit aperture proximate the exit aperture of said mitral valve lead; and
    wherein an inflatable balloon is secured in fluid communication with the exit aperture of said air port to positively locate said mitral valve lead proximate a left atrial wall and an atrioventricular groove of said heart tissue when inflated.

6. An apparatus for bipolar radio frequency ablation as claimed in claim 1 wherein a portion of a conductive surface of said mitral valve slide is capable of contacting said heart tissue, wherein said conductive surface of said mitral valve slide is in electrical contact with the electrically conductive surface of said mitral valve lead.

7. An apparatus for bipolar radio frequency ablation as claimed in claim 6 wherein said mitral valve slide conductive portion forms an uninterrupted conductive surface with said mitral valve lead conductive surface.

8. An apparatus for bipolar radio frequency ablation as claimed in claim 1 further comprising:
    a plurality of rod guides extending from said epicardial lead; and
    a plurality of control rods engaging said rod guides to aid in the placement of said epicardial lead and said mitral valve slide.

9. An apparatus for bipolar radio frequency ablation as claimed in claim 8 wherein said mitral valve slide comprises:
    a plurality of apertures for accepting an end of said plurality of control rods.

10. An apparatus for bipolar radio frequency ablation as claimed in claim 1 wherein said mitral valve slide comprises:
a central irrigation port for accepting a source of irrigation fluid, said irrigation port in fluid communication with a plurality of irrigation passages in said mitral valve slide for delivery of irrigation fluid to a plurality of points proximate said epicardial lead.

11. An apparatus for bipolar radio frequency ablation as claimed in claim 10 wherein one of said irrigation passages is in fluid communication with the exterior surface of said epicardial lead for delivery of irrigation fluid.

12. An apparatus for bipolar radio frequency ablation as claimed in claim 10 wherein one of said irrigation passages is in fluid communication with the ablating surface of said epicardial lead for delivery of irrigation fluid.

13. An apparatus for bipolar radio frequency ablation as claimed in claim 10 wherein one of said irrigation passages is in fluid communication with a plurality of points along a surface of said mitral valve slide in contact with said heart tissue.

14. An apparatus for bipolar radio frequency ablation as claimed in claim 1 comprising:
an endocardial catheter containing an ablating lead having an ablating surface at a distal end thereof for conducting radio frequency energy between said epicardial lead conductive surface and said ablating lead ablating surface.

* * * * *